United States Patent [19]

Hartwell et al.

[11] 4,197,414

[45] Apr. 8, 1980

[54] AMINE-RESIN SUPPORTED RHODIUM-COBALT BIMETALLIC CLUSTERS AS NOVEL HYDROFORMYLATION CATALYSTS

[75] Inventors: George E. Hartwell, Framingham; Philip E. Garrou, Holliston, both of Mass.

[73] Assignee: The Dow Chemical Company, Midland, Mich.

[21] Appl. No.: 952,505

[22] Filed: Oct. 18, 1978

Related U.S. Application Data

[62] Division of Ser. No. 803,815, Jun. 6, 1977, Pat. No. 4,144,191.

[51] Int. Cl.$^2$ ............................................. C07C 29/00
[52] U.S. Cl. ...................................... 568/909; 560/263; 568/820; 568/831; 568/816; 568/832; 568/852
[58] Field of Search ............... 568/909, 820, 831, 832, 568/852; 560/263

[56] References Cited

U.S. PATENT DOCUMENTS

| | | | |
|---|---|---|---|
| 3,488,333 | 1/1970 | Lefebvre et al. | 252/431 N |
| 3,594,425 | 7/1971 | Brader et al. | 568/909 |
| 3,636,159 | 1/1972 | Solomon | 252/431 N |
| 4,072,720 | 2/1978 | Haag et al. | 568/909 |

*Primary Examiner*—Joseph E. Evans
*Attorney, Agent, or Firm*—G. R. Plotecher

[57] ABSTRACT

Olefins are converted to alcohols by a one-step, hydroformylation process comprising contacting an olefin, such as 1-hexene, with a gaseous mixture of carbon monoxide and hydrogen in the presence of a catalyst prepared by loading a bimetallic cluster of the formula: $Rh_xCo_yCO_{12}$ wherein both x and y are independently integers 1–3 with the proviso that $\Sigma(x+y)=4$, onto an amine resin, such as Dowex ® MWA-1.

11 Claims, No Drawings

AMINE-RESIN SUPPORTED RHODIUM-COBALT BIMETALLIC CLUSTERS AS NOVEL HYDROFORMYLATION CATALYSTS

CROSS REFERENCE TO RELATED APPLICATION

This is a division of application Ser. No. 803,815, filed June 6, 1977, now U.S. Pat. No. 4,144,191.

BACKGROUND OF THE INVENTION

1. Field of the Invention

This invention relates to multinuclear metal catalysts. In one aspect, the invention relates to said catalysts supported by an amine resin. In other aspects, the invention relates to a method of preparing and to various methods of employing these supported catalysts.

2. Description of the Prior Art

The art-recognized method (I) of preparing alcohols from olefins is a two-step oxo or hydroformylation process:

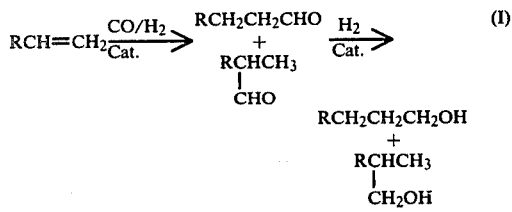

The first step comprises contacting at elevated temperature and pressure, e.g., 125° C.–175° C. and about 3000–5000 psi, an olefin with synthesis gas (a gaseous mixture of hydrogen and carbon monoxide) in the presence of an oxo catalyst to produce a mixture of aldehydes. These aldehydes are then hydrogenated (typically in the presence of a hydrogenation catalyst) in a second step to their corresponding alcohols. Cobalt and rhodium are frequently used as the oxo catalysts.

Reported efforts to convert this two-step process to a highly selective one-step process have been singularly unsuccessful. Slaugh et al., *J. Organometal. Chem.*, 13, 469 (1968), teach that a catalyst comprising cobalt carbonyl and a modifying ligand of tributyl phosphine affords a one-step, oxo synthesis of alcohols but accompanying olefin hydrogenation reduces yields (77 percent alcohol). Jurewicz et al., *Adv. Chem. Ser.*, 132, 240-51 (1974) and Rollmann et al., Ger. Pat. No. 2,357,645, teach respectively that rhodium carbonyl supported on an amine resin or in the presence of tertiary amines also catalyzes a one-step oxo synthesis of alcohols. However, here too both research teams report suppressed yields (about 28 percent alcohol).

SUMMARY OF THE INVENTION

According to this invention, olefins are converted to alcohols by a one-step oxo process comprising contacting the olefin with a gaseous mixture of hydrogen and carbon monoxide at a temperature of at least about 50° C. and a pressure of at least about 500 psi in the presence of a catalytic amount of a catalyst consisting essentially of a rhodium-cobalt bimetallic cluster supported on an amine resin. These catalysts are both easily prepared (by contacting the bimetallic cluster with an amine resin in an inert liquid medium) and exhibit long life. Moreover, these catalysts are highly selective (generating alcohols in essentially quantitative yield) and permit the oxo process to be conducted at less rigorous process conditions.

DETAILED DESCRIPTION OF THE INVENTION

The supported catalysts here used are prepared by loading onto an amine resin a bimetallic cluster of the formula:

wherein x and y are individually integers of 1–3 with the proviso that $\Sigma(x+y)=4$. These bimetallic clusters are tetranuclear carbonyls and are readily synthesized by any number of varying methods. For example, tetranuclear carbonyl $Rh_2Co_2(CO)_{12}$ can be prepared by either of the following methods (III, IV):

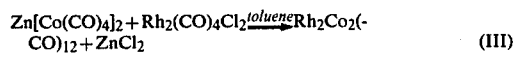

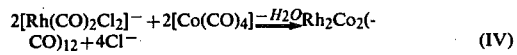

These and other methods for preparing the bimetallic clusters of this invention are further described by Martinengo et al., *J. Organometal. Chem.*, 59, 379 (1973). Conventional methods for preparing the monometallic carbonyls, e.g. $Zn[Co(CO)_4]_2$, etc., are described by King, *Organometallic Synthesis*, 1, 98–101 (1965). Clusters wherein x and y are each 2 are preferred.

Any amine resin that can be loaded with the bimetallic cluster (II) can be used in the practice of this invention. These resins are typically cross-linked and essentially water insoluble, and they comprise primary, secondary and/or tertiary integral and/or pendant amine functionally. By "integral" amine functionality is meant that the amine functionality, i.e., amino group, is incorporated directly into the resin matrix. Examples of such resins include: Polyethylenepolyamine cross-linked with epichlorohydrin, urea-formaldehyde cross-linked copolymers, melamine-formaldehyde cross-linked copolymers, etc. By "pendant" amine functionality is meant that the amine functionality is suspended from the resin matrix (backbone). This resin backbone can be varied to convenience and can comprise essentially any cross-linked composition, such as styrene-divinylbenzene, styrene-glycoldimethacrylate, aniline-formaldehyde, aryl/polyamine-formaldehyde, phenol-formaldehyde, polyacrylate, etc. The pendant amine functionality can also vary to convenience and includes such diverse functionality as primary, secondary and tertiary amines, di-, tri- and polyamines, hydrolyzed oxazolines, etc. Examples of such resins, all commercially available and described generally as weak-base anion exchange resins, include: Dowex ® MWA-1, WGR and 44 (manufactured by The Dow Chemical Company); Amberlite ® IRA-45, 68 and 93 (manufactured by Rohm & Haas Company); Duolite ® A-7 and A-14 (manufactured by Diamond Alkali Company); and Ionac ® A-260 (manufactured by Ionac Chemical Corporation).

The amine resins of this invention can take many forms, but swellable gel or macroporous beads are the most common and are thus preferred. Resins having pendant amine functionality are preferred to resins having integral amine functionality and resins having an exchange capacity of at least about 3 milliequivalents per gram of dry resin are particularly preferred. These latter resins include resins comprising a cross-linked polymer matrix having pendant amine functionality of the formulae —N(R)$_2$ and/or —NHR'N(R)$_2$ wherein each R is individually hydrogen or C$_1$-C$_6$ alkyl, R' is C$_2$-C$_6$ alkylene, and the open valence is the bond that joins the functionality to the polymer matrix. Typical substituents include: R alkyls, such as methyl, ethyl, propyl, isopropyl, butyl, etc.; and R' alkylenes, such as ethylene, propylene, hexylene, etc. The radical —NHR'N(R)$_2$ represents various diamines and alkyl-substituted diamines such as:

| —NHR'N(R)$_2$ | R' | N(R)$_2$ |
|---|---|---|
| ethylenediamine | —CH$_2$CH$_2$— | NH$_2$ |
| propylenediamine | —CH$_2$CH$_2$CH$_2$— | NH$_2$ |
| hexylenediamine | —CH$_2$(CH$_2$)$_4$CH$_2$— | NH$_2$ |
| N-methylethylene-diamine | —CH$_2$CH$_2$— | NHCH$_3$ |
| N,N-dimethylethylene-diamine | —CH$_2$CH$_2$— | N(CH$_3$)$_2$ |
| N,N-ethylmethyl-ethylenediamine | —CH$_2$CH$_2$ | N(CH$_3$)(CH$_2$CH$_3$) |

The amine functionality of these preferred resins can be either primary, secondary and/or tertiary although primary functionality is preferred when the amine is of the formula —NHR'N(R)$_2$ and secondary and tertiary functionality is preferred when the amine is of the formula —N(R)$_2$. —N(R)$_2$ functionality is preferred to —NHR'N(R)$_2$ functionality. An especially preferred, commercial amine resin is Dowex ® MWA-1 (comprising a macroporous, cross-linked polystyrene polymer matrix having pendant amine functionality of the formula —N(R)$_2$ wherein each R is methyl).

The catalyst of this invention is prepared by loading the bimetallic cluster onto the amine resin. This loading is accomplished by a method comprising contacting in an inert liquid medium the bimetallic cluster with the amine resin. Typically, the contacting is conducted at a cluster:amine on resin mole ratio (i.e., cluster:resin mole equivalents ratio) of at least about 1:100 and preferably at least about 1:25. The maximum cluster:resin mole equivalents ratio can be varied as desired but is typically about 1:1 and preferably about 1:4.

The inert liquid medium can comprise one or more liquid solvent(s) in which the bimetallic cluster is soluble and which is inert (non-reactive) with both the method reagents and products. Aliphatic and aromatic hydrocarbons and substituted hydrocarbons are illustrative solvents and include such compounds as: Hexane, benzene, toluene, xylene, o-dichlorobenzene, methylene chloride, chloroform, carbon tetrachloride, etc. The aromatic and substituted aromatic hydrocarbons are preferred with benzene and toluene especially preferred.

This method can be practiced at any temperature and pressure at which the reaction mixture of bimetallic cluster and solubilizing inert liquid medium are liquid. Convenience prefers ambient temperature and pressure, e.g., 20°–30° C. and atmospheric pressure. The contacting (loading) is typically conducted under an inert atmosphere, such as argon, etc. and for a sufficient period of time to load the bimetallic cluster onto the resin. This period of time will vary with the method reagents and conditions employed but with many reagents and at ambient conditions the loading is significantly commenced after about 2 hours, and is generally complete after about 12 hours. The resulting catalyst is recovered by any convenient physical separation technique, e.g., filtering.

The physical and chemical structure of the catalyst, i.e., the bimetallic cluster loaded (supported) upon the amine resin, is not fully known. However, it is known that the catalyst comprises rhodium and cobalt carbonyl attached to the amine resin. Typically, the catalyst comprises, as determined by any conventional elemental analysis method, at least about 1 weight percent, and preferably at least about 4 weight percent, rhodium (metal basis) and at least about 0.5 weight percent, and preferably at least about 2.5 weight percent, cobalt (metal basis). Resin saturation is the only limitation upon the maximum weight percent of rhodium and cobalt and the saturation levels are preferred for reasons of catalytic activity and life. Of course, saturation levels vary dependent upon the particular amine resin and bimetallic cluster employed.

These new catalysts are used in substantially the same manner as known catalysts. This invention's oxo process of converting olefins directly to alcohols requires a catalytic amount of catalyst. Typically, the minimum amount of catalyst (Rh-Co metal basis) present is about 0.1 weight percent, and preferably about 0.25 weight percent, based on the weight of olefin. Again, practical considerations such as economy and convenience are the only limitations upon the maximum amount of catalyst that can be present, although these considerations prefer a maximum amount of about 5 weight percent, and most preferably of about 2 weight percent. Conventional oxo process (reaction) times are employed.

While these catalysts are operable under typical oxo temperatures and pressures (about 125° C.–175° C. and 3000–5000 psi), they are also operable at much lower temperatures and/or pressures. Accordingly, in the presence of the catalysts here used, olefins are directly converted to alcohols at method parameters of at least about 50° C. and at least about 500 psi. However, in most instances best results are achieved at method parameters of at least about 100° C. and 750 psi and thus these latter parameters are preferred. Practical limitations, such as reagent and product degradation, convenience, etc. are the only limitations on the maximum method parameters. Obviously, different olefins can require different parameters.

Any olefin that can be converted to an aldehyde by the known oxo process can be converted to an alcohol by this invention's oxo process. Illustrative oxo olefins include: Ethylene, propylene, 1-butene, 2-butene, 1-pentene, 1-hexene, 1-decene, 3-methyl-1-butene, butadiene, 1,4-pentadiene, isoprene, cyclohexene, cycloheptene, dicyclopentadiene, norborene, allyl alcohol, allyl acetate, etc. Suitable combinations of different olefins, such as ethylene and propylene, can also be used.

The synthesis gas used in the known oxo processes comprises a gaseous mixture of hydrogen and carbon monoxide. Any conventional mixture of these two compounds can be used in the instant process although amounts in excess of stoichiometric oxo process requirements are preferred.

The following examples are illustrative of certain specific embodiments of this invention. Unless indicated to the contrary, all parts and percentages are by weight.

SPECIFIC EMBODIMENTS

Example 1

Catalyst Preparation

Dowex® MWA-1 beads (0.25 g), (an amine resin manufactured by The Dow Chemical Company and comprising a cross-linked polystyrene backbone having pendant benzyl dimethylamine functionality), a bimetallic cluster of the formula: $Rh_2Co_2(CO)_{12}$ (0.2 g) and toluene (20 ml) were mixed and agitated under argon at ambient conditions for 12 hours. The modified beads (catalyst) were then filtered and dried under vacuum. The catalyst had a gray-black color when wet with toluene and a grayish color when dry. Galbraith Elemental Analysis showed the catalyst to comprise about 4 weight percent rhodium and about 2.6 weight percent cobalt and gave an infrared spectrum exhibiting several overlapping strong absorptions at about 1890 $cm^{-1}$, a strong absorption at about 2000 $cm^{-1}$ and a medium absorption at about 2010 $cm^{-1}$ in the carbonyl stretching frequency region.

Example 2

The catalyst (0.2 g) prepared in Example 1 was charged to an Aminco Shaking Pressure Reactor with dry, deaerated benzene (3 ml) under argon. 1-Hexene (1 ml) was then added and the reactor contents subsequently flushed with nitrogen and pressured with equimolar amounts of carbon monoxide and hydrogen. The reactor was heated to about 100° C., with a pressure of about 750 psi, and held thereat for 2 hours. The reactor was then allowed to cool and the contents analyzed by both gas chromatography (GC) and $^1H$ nuclear magnetic resonance (NMR). The reaction product contained 96.3 percent alcohol.

Control A

A catalyst was prepared according to the procedure of Example 1 except that $Rh_4(CO)_{12}$ was substituted for the bimetallic cluster and the catalyst comprised 9.2 percent Rh rather than 6.6 percent Rh-Co. Example 2 was then repeated except that the catalyst thus prepared was substituted for the catalyst prepared in Example 1 and a pressure of 1,000 psi was substituted for 750 psi. GC analysis of the reaction product showed aldehydes present to the extent of 21 percent and alcohols present to the extent of only 54.4 percent.

Control B

A catalyst was prepared according to the procedure of Example 1 except that $Co_4(CO)_{12}$ was substituted for the bimetallic cluster and the catalyst comprised 3 percent Co rather than 6.6 percent Rh—Co. Example 2 was then repeated except that the catalyst thus prepared was substituted for the catalyst prepared in Example 1 and a pressure of 1,000 psi was substituted for 750 psi. GC analysis of the reaction product showed aldehydes present to the extent of 71.1 percent with only 1.2 percent alcohol present.

The results of Controls A and B demonstrate the marked difference between supported Rh and Co monometallic clusters and supported Rh—Co bimetallic clusters.

Control C

A catalyst was prepared according to the procedure of Example 1 except that $Rh_6(CO)_{16}$ and $Co_2(CO)_8$ at a 1:1 metal ratio were substituted for the bimetallic cluster. Example 2 was then repeated except that the catalyst thus prepared was substituted for the catalyst prepared in Example 1, a pressure of 1,000 psi was substituted for 750 psi, and a residence time of 3 hr was substituted for 2 hr. GC analysis of the reaction product showed aldehydes present to the extent of 83 percent. This demonstrates the pyrotechnic contrast between a catalyst prepared from an Rh-Co bimetallic cluster and a catalyst prepared from individual Rh and Co carbonyls.

Control D

Following a procedure similar to Example 2, 1-hexene (1 ml) was charged to a reactor containing dry deaerated benzene (3 ml) and a mixture of benzyl dimethylamine and $Rh_2Co_2(CO)_{12}$. The mixture comprised about 6.5 weight percent metal as did the catalyst of Example 2. The reactor contents were then flushed with nitrogen and pressured with equimolar amounts of carbon monoxide and hydrogen and heated to 100° C., the pressure reaching 1,000 psi. The reactor contents were held thereat for 3 hours, allowed to cool and subsequently analyzed. The reaction product contained 71.9 percent aldehydes, 12.1 percent alcohols and the remainder a mixture of isomerization products. This demonstrates the marked different between an Rh-Co bimetallic cluster supported by an amine resin and an Rh-Co bimetallic cluster merely in the presence of amine functionality.

Examples 3–5

Control D was repeated except the catalyst of Example 1 was substituted for the catalyst of Control D and various olefins were substituted for 1-hexene. The results are tabulated below.

TABLE I

| Olefins to Alcohols via Oxo Process Catalyzed by $Rh_2Co_2(CO)_{12}$ Supported on Dowex$^R$ MWA-1 | | | |
|---|---|---|---|
| Ex | Olefin | Conversion (%) | Alcohol (%) | Aldehyde (%) |
| 3 | Cyclohexene | 78 | 85 | 0 |
| 4 | Allyl Alcohol | 100 | 100 | 0 |
| 5 | Allyl Acetate | 100 | 100 | 0 |

The product alcohols of Examples 4 and 5 included cleavage products, i.e., some allyl alcohol and allyl acetate underwent hydrogenolysis (V) to propene and propene was then hydroformulated (VI).

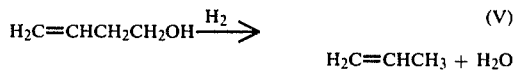

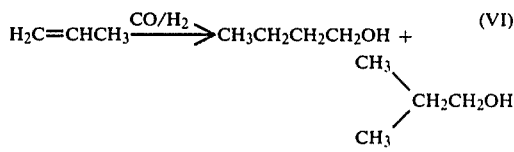

Example 6

The procedure of Example 2 was again repeated except toluene was substituted for benzene, dicyclopentadiene was substituted for 1-hexene and the reactor contents were heated to 125° C. with the pressure reaching 1,500 psi and the contents were held thereat for 5 hours. Analysis showed a quantitative conversion of the olefin to dimethanoldicyclopentadiene.

Although the invention has been described in considerable detail through the preceding specific embodiments, it is to be understood that these embodiments are for purposes of illustration only. Many variations and modifications can be made by one skilled in the art without departing from the spirit and scope of the invention.

What is claimed is:

1. A one-step oxo process for converting olefins to alcohols, the process comprising contacting the olefin with a gaseous mixture of carbon monoxide and hydrogen at a temperature of at least about 50° C. and a pressure of at least about 500 psi in the presence of a catalytic amount of a catalyst consisting essentially of a rhodium-cobalt bimetallic cluster loaded on an amine resin.

2. The process of claim 1 wherein the contacting is conducted at a temperature of at least about 100° C. and a pressure of at least about 750 psi.

3. The process of claim 2 wherein the catalyst, Rh—Co metal basis, is present in an amount of at least about 0.1 weight percent based upon the weight of olefin.

4. The process of claim 3 wherein the catalyst is present in an amount between about 0.25 and about 5 weight percent, inclusive, based upon the weight of olefin.

5. The process of claim 4 wherein the catalyst is prepared by loading onto an amine resin a bimetallic cluster of the formula: $Rh_xCo_y(CO)_{12}$ wherein x and y are individually integers of 1-3 with the proviso that $\Sigma(x+y)=4$.

6. The process of claim 5 wherein the amine resin comprises a cross-linked polymer matrix having pendant amine functionality of the formulae $-N(R)_2$ and/or $-NHR'N(R)_2$ wherein each R is individually hydrogen or $C_1-C_6$ alkyl, R' is $C_2-C_6$ alkylene, and the open valence is the bond that joins the functionality to the polymer matrix.

7. The process of claim 6 wherein x and y are each 2.

8. The process of claim 7 wherein the pendant amine functionality is of the formula $-N(R)_2$.

9. The process of claim 8 wherein the resin comprises a cross-linked polystyrene matrix and each R is methyl.

10. The process of claim 9 wherein the catalyst comprises at least about 1 weight percent rhodium and at least about 0.5 weight percent cobalt.

11. The process of claim 10 wherein the olefin is 1-hexane.

* * * * *